US010379104B2

(12) United States Patent
Ritter et al.

(10) Patent No.: US 10,379,104 B2
(45) Date of Patent: Aug. 13, 2019

(54) EXPOSURE APPARATUS

(71) Applicant: Fraunhofer-Gesellschaft zur Foerderung der angewandten Forschung e.V., Munich (DE)

(72) Inventors: Detlef Ritter, Hannover (DE); Jan Knebel, Hannover (DE)

(73) Assignee: Fraunhofer-Gesellschaft zur Foerderung der angewandten Forshcung e.V., Munich (DE)

(*) Notice: Subject to any disclaimer, the term of this patent is extended or adjusted under 35 U.S.C. 154(b) by 699 days.

(21) Appl. No.: 14/914,139

(22) PCT Filed: Apr. 29, 2014

(86) PCT No.: PCT/DE2014/100312
§ 371 (c)(1),
(2) Date: Feb. 24, 2016

(87) PCT Pub. No.: WO2015/027998
PCT Pub. Date: Mar. 5, 2015

(65) Prior Publication Data
US 2016/0216250 A1   Jul. 28, 2016

(30) Foreign Application Priority Data
Aug. 30, 2013   (DE) .................. 10 2013 109 450

(51) Int. Cl.
*B01L 3/00*       (2006.01)
*G01N 33/50*     (2006.01)

(52) U.S. Cl.
CPC ...... *G01N 33/5008* (2013.01); *B01L 3/50853* (2013.01); *B01L 2200/026* (2013.01);
(Continued)

(58) Field of Classification Search
CPC .......... B01L 3/50853; B01L 2300/041; B01L 2300/048; B01L 2300/049; B01L 2200/026; B01L 2300/0829
See application file for complete search history.

(56) References Cited

U.S. PATENT DOCUMENTS

| 4,762,794 A | 8/1988 | Nees |
| 5,019,348 A * | 5/1991 | Ohms .................... C07K 1/128 422/116 |

(Continued)

FOREIGN PATENT DOCUMENTS

| DE | 33 17 551 A1 | 11/1984 |
| DE | 195 26 533 A1 | 1/1997 |

(Continued)

OTHER PUBLICATIONS

Ritter, D. et al.: "Investigations of the Biological Effects of Airborne and Inhalable Substances by Cell-Based In Vitro Methods: Fundamental Improvements to the ALI Concept," Advances in Toxicology, vol. 2014, Nov. 12, 2014, pp. 1-11.
(Continued)

*Primary Examiner* — Lyle Alexander
*Assistant Examiner* — Dwayne K Handy
(74) *Attorney, Agent, or Firm* — Collard & Roe, P.C.

(57) ABSTRACT

An exposure apparatus for carrying out in vitro experiments with biological test systems, which are perfused with an exposure medium, forming an exposure atmosphere, includes an exposure cap, which is dimensioned in such a manner that it can be set onto a standard multiwell plate and connected with the standard multiwell plate using suitable connecting elements.

52 Claims, 6 Drawing Sheets

Figure 1:
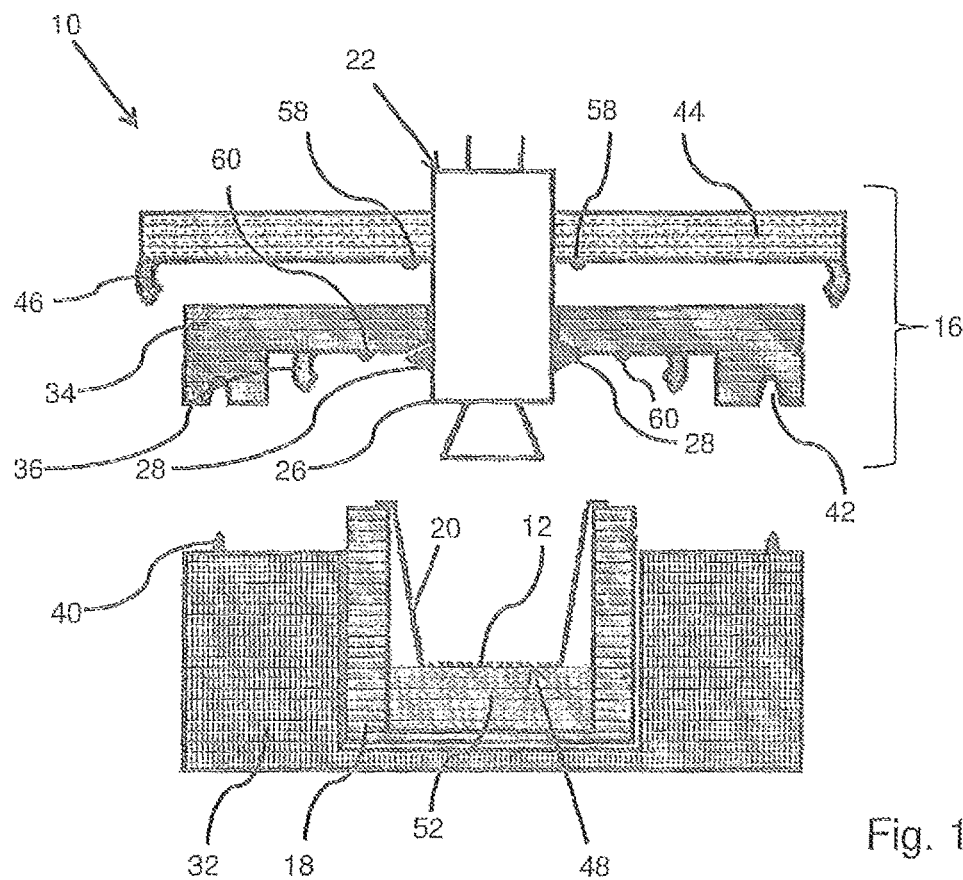

(52) U.S. Cl.
CPC . *B01L 2200/0689* (2013.01); *B01L 2300/048* (2013.01); *B01L 2300/0829* (2013.01); *B01L 2300/10* (2013.01)

(56) References Cited

U.S. PATENT DOCUMENTS

| | | | |
|---|---|---|---|
| 5,863,792 | A | 1/1999 | Tyndorf et al. |
| 6,485,690 | B1 * | 11/2002 | Pfost .................. B01J 19/0046 422/552 |
| 6,908,767 | B2 | 6/2005 | Bader |
| 8,426,157 | B2 | 4/2013 | Knebel et al. |
| 8,501,462 | B2 | 8/2013 | Eddington et al. |
| 9,096,824 | B2 | 8/2015 | Mohr et al. |
| 2005/0260745 | A1 | 11/2005 | Domansky et al. |
| 2010/0009335 | A1 | 1/2010 | Joseph et al. |
| 2010/0129850 | A1 * | 5/2010 | Knebel .................. C12M 25/04 435/29 |
| 2010/0273246 | A1 | 10/2010 | Fukano et al. |

FOREIGN PATENT DOCUMENTS

| | | |
|---|---|---|
| DE | 10 2007 030 413 A1 | 1/2009 |
| DE | 10 2009 039868 A1 | 3/2011 |
| WO | 02/24861 A2 | 3/2002 |
| WO | 2005/123950 A2 | 12/2005 |
| WO | 2010/040473 A2 | 4/2010 |

OTHER PUBLICATIONS

Domansky, K. et al. "Perfused Multiwell Plate for 3D Liver Tissue Engineering." Lab Chip, Jan. 7, 2010; 10(1). 18 pages.
ANSI/SLAS Jan. 2004: Microplates—Footprint Dimensions, Oct. 12, 2011.
ANSI/SLAS Feb. 2004: Microplates—Height Dimensions, Oct. 13, 2011.
ANSI/SLAS Mar. 2004: Microplates—Bottom Outside Flange Dimensions, Oct. 13, 2011.
ANSI/SLAS Apr. 2004: Microplates—Well Positions, Oct. 13, 2011.
ANSI/SLAS Jun. 2012: Microplates—Well Bottom Elevation, Oct. 13, 2011.
International Search Report of PCT/DE2014/100312, dated Jan. 30, 2015.

* cited by examiner

EXPOSURE APPARATUS

CROSS REFERENCE TO RELATED APPLICATIONS

This application is the National Stage of PCT/DE2014/100312 filed on Aug. 29, 2014, which claims priority under 35 U.S.C. § 119 of German Application No. 10 2013 109 450.3 filed on Aug. 30, 2013, the disclosure of which is incorporated by reference. The international application under PCT article 21(2) was not published in English.

The invention relates to an exposure apparatus for carrying out in vitro experiments with technical replicates of at least one biological test system, to which replicates an exposure medium can be applied by perfusion, forming an exposure atmosphere on or above the biological test system.

When carrying out in vitro experiments with biological test systems, particularly with cells, cell cultures or tissues, a substance is usually brought into contact with the biological test system—independent of the goals of the experiments or of the studies; this is called exposure.

During this process, the biological test system or biological testing system is exposed to an exposure atmosphere, which is formed by an exposure medium. The exposure medium can contain and/or form the substance, which is also referred to as a test substance or testing substance. In some cases, it can be desirable if the exposure medium is configured without a substance, i.e. without a test substance or testing substance.

The biological test system can be a eukaryote culture, particularly preferably cell lines, primary cell isolates, tissue sections, reconstructed tissue such as co-cultures, or genetically modified cells, or a prokaryote culture.

The exposure medium can be liquid or gaseous.

The gaseous exposure medium can be present as a pure gas or as a gas mixture, i.e. ail the substances contained in it, particularly atoms, molecules, etc., are in the gas phase, and/or it can also serve as a carrier for solid substances and/or liquid substances. In particular, in this way aerosols, atomized liquids, small liquid droplets (for example plant protection agents as a spray mist, etc.), suspended particles, solid particles (for example wood dust, etc.), gaseous suspensions, atomized suspensions or emulsions can be contained in the carrier gas as the substances to foe carried.

The said in vitro experiments can be targeted manipulations by means of pharmacologically active substances. However, the said in vitro experiments can also be experiments that are supposed to influence cell growth or differentiation, for example within the scope of what are called tissue engineering techniques. Also, the said in vitro experiments can be toxicological studies of the most varied substances or materials.

With regard to the manner in which the substances are brought into contact with the biological test systems, a distinction can fundamentally be made between two methods of working, namely static exposure, for one thing, and dynamic exposure, for another; the latter is also referred to as perfusion or perfusive exposure.

In the case of static exposure, the substance is applied to the biological test system once or also repeatedly, particularly additively, but not continuously; it then remains on the system, for a certain period of time without being replaced.

In the case of dynamic exposure, the substance is continuously fed in and conducted away, for example in order to produce greater effectiveness or sensitivity during the study, or also because of physical/chemical or other properties of the test substances of the biological test system or other boundary conditions of the study.

Possibilities for carrying out static exposures are implemented in many different ways and are commercially available in a broad selection. Usually, in this regard, the substance, which is incorporated into a buffer or culture medium, particularly suspended or dissolved, is placed into a well or a depression or a cavity of a multiwell plate, in which the biological test system is also situated.

In contrast, possibilities for carrying out dynamic exposures are available in less varied manner.

For carrying out dynamic exposures or perfusion exposures with liquid exposure media, apparatuses are disclosed, for example, in WO 2005/123950 A2, in DE 33 17 551 A1, or also by Domansky et al. in Lab Chip (2010), 10, 51-58.

For carrying out dynamic exposures or perfusion exposures with gaseous exposure media, apparatus are disclosed in DE 195 26 533 US 2010/0273246 A1, WO 2010/040473 A2 or DE 10 2007 030 413 which stems from the inventors of the present patent application.

All of these apparatuses have in common that they represent special solutions that sire not easily compatible with the usual standard equipment of a laboratory, and therefore cannot be integrated into established work sequences in time-saving and cost-saving manner.

Beyond this, ail of the apparatuses for carrying out dynamic exposures or perfusion exposures with gaseous exposure media—with the exception of the apparatus disclosed in DE 10 2007 030 413 A1—have the disadvantage that they technically permit mixing of the two fluid phases that are present.

According to the state of the art, the fluid phases are, on the one hand, the liquid phase in the form of the maintenance medium or nutrient medium, which is brought up to the culture vessels that contain the biological test system, from the underside, in order to maintain the biological test system, and, on the other hand, the gaseous phase in the form of the exposure medium or exposure atmosphere, in which the substance, i.e. the test substance or testing substance, is brought up to the biological test system in gaseous form or carried by air. Mixing has many different disadvantageous consequences in the study; these result in a lack of reproducibility, production of undesirable by-products, and an insufficiently defined (testing) situation of the biological test system.

Here and in the following, a maintenance medium in the sense of the invention is understood to be a culture medium, also called a nutrient medium, with or without additives, or a saline solution.

Aside from the aforementioned apparatuses for carrying out dynamic exposures or perfusion exposures, apparatuses for targeted cell cultivation are known. Preferably, it is supposed to be possible to adjust the culture conditions that promote growth of the cells in automated manner, using such apparatuses.

For example, an apparatus for automated culturing and/or treatment of cells for diagnostic purposes is known from WO 02/24861 A2; this apparatus has a multiwell plate having a plurality of wells, in which cells are accommodated. In this regard, the wells are supposed to have nutrients and/or oxygen, flew through them from the top, thereby promoting growth of the cells. No separate culture vessels, called inserts, are accommodated in the wells themselves.

An insert is introduced into each well to allow flow through it; this insert has a inflow bore and a return flow bore. The insert has a separation crosspiece between the inflow bore and the return flow bore on the side directed toward the bottom of the well, so that the nutrients introduced by way of the inflow bore cannot flow directly to the return flow bore, in the manner of a short-circuit. To seal the well, each insert is provided with a sealing ring on the circumference side.

In place of inserts that can be introduced into the wells, a cover plate having inflow connectors and return flow connectors inserted, in it can also be provided, wherein an inflow connector and a return flow connector are assigned to each well. In this regard, the inflow connector projects deeper into the well than the return flow connector, in order to prevent the aforementioned short-circuit here, too. The cover plate can be connected with the cell culture plate by being screwed onto it. In place of or in addition to this connection, a seal can also be achieved by means of a sealing device between cover plate and cell culture plate.

According to WO 02/24861 A2, the cover plate can be configured in two parts, with an upper and a lower cover, wherein the upper and the lower cover can be connected with one another in distance-adjustable manner. A bias can be achieved by means of springs disposed in between. The upper cover is set onto the edges of the cell culture plate, on its circumference, by way of crosspieces at its edges. The inflow connectors and return flow connectors are pushed by means of the lower cover, wherein these accordingly are also conducted out through the upper cover, either on its top or, if necessary, also laterally. Sealing of the wells is supposed to be achieved by means of the springs, in that the lower cover is correspondingly pressed tightly onto the top of the cell culture plate. At the same time, in this manner, attachments that project downward on the underside of the lower cover, from the cover, are introduced into the wells to form closed cell culture spaces. For one thing, the lower cover therefore rests on the edges of the wells, and for another, it is introduced into the wells by way of the attachments.

An arrangement composed of a multiwell plate and an insert plate having multiple inserts is known from U.S. Pat. No. 8,501,462 B2. Multiwell plate and insert plate can be connected with one another, wherein each insert of the insert plate can be positioned in a well of the multiwell plate. In this regard, the insert plate lies on the multiwell plate.

Each insert has a feed-in connector that can be connected with a gas supply source, and an outlet connector. Multiple feed-in connectors can be connectable with the gas supply source by way of a gas manifold. Multiple feed-in connectors can accordingly have a common gas supply line. Multiple outlet connectors can be connected with a common gas outlet line. At the bottom of each insert, a membrane that is gas-permeable from below is attached at a predetermined distance from the bottom of the insert, thereby causing a flow channel to be formed between bottom and gas-permeable membrane, which channel forms a flow connection between the feed-in connector and the outlet connector. Multiple flow channels that can connect the inlet connector and the outlet connector can also be formed between bottom and gas-permeable membrane, if the gas-permeable membrane has multiple projections that are directed upward, the tops of which projections are connected with the bottom of the insert. The number, placement, and the extent of the projections determine the progression of the flow channel(s) as well as the distance of the membrane from the bottom of the insert.

Bach gas-permeable membrane of the insert disposed in a well is furthermore disposed at a predetermined distance from the base surface of the well. Each insert can furthermore have a separate media inlet and media outlet, which stand in a flow connection with one another, wherein a flow channel forms between the gas-permeable membrane of the insert and the base surface of the well. For the intended application cases, cells are cultured on the base surface of a well, and brought into contact with a gas that influences the growth of the cells, which gas diffuses through the gas-permeable membrane of the insert. For this purpose, the arrangement is situated in an incubator.

U.S. Pat. No. 5,863,792 discloses an apparatus for culturing of cells or tissue cultures in vitro. The apparatus has a multiwell plate as well as a removable lid. The lid serves to prevent the loss of cells or samples from the wells of the multiwell plate, to protect the content of the multiwell plate from the environment, and to protect the user from the content of the multiwell plate, if the plate contains a material that is harmful or potentially harmful. Furthermore, means for removable attachment of the lid to the plate are provided, by means of which a sealing material situated along the inner edge circumference of the lid is compressed between lid and multiwell plate, and the interior of the multiwell plate is protected from the external environment, and as a result, the multiwell plate is made available in a biologically secure environment.

US 2010/0009335 A1 discloses an apparatus for in vitro cultivation of cells or tissue cultures in a growth medium. The apparatus comprises a multiwell plate, in the wells of which cells or tissue are cultivated, wherein devices are provided for isolating the wells of the apparatus with regard to the environment, in order to control the temperature of the growth medium, to obtain a view of the cells or the tissue culture within a well, and to obtain control or regulation of the growth conditions within a well, including controlled regulation and monitoring of the medium gases conducted into and out of the well, for example, such as O2, CO2 or N2, of the pH value that is present there, or of the temperature that prevails there.

The multiwell plate comprises a micro heating element, which is configured in such a manner that it controls the temperature of one or more wells or of a growth medium for optimization of the growth conditions, and thereby it is possible to do without a separate incubator.

The apparatus also comprises a lid that can be set onto the multiwell plate, wherein a further micro heating element can be provided, in order to control the temperature of the lid. In this regard, the temperature of the lid is supposed to be higher than the temperature of the well, in order to prevent condensation on the lid.

One or more than one seal, advantageously in the form of an O-ring, can be provided between lid and each well, in order to seal off the edge of the wells and to prevent uncontrolled material exchange between the wells. The seal is also supposed to contribute to maintaining the micro-environment that is formed within each well, or to achieving biological isolation of each well.

The lid can be attached to the wells, by means of a click-on connection or clamping connection, and can have the devices mentioned above.

The apparatus can furthermore have a plurality of ports, which stand in connection with one or more wells. At least some of the ports can be configured as septum ports, in order to allow sample-taking without canceling out the seal or the biological isolation of a well.

Furthermore, the ports can be designed in such a manner that media, for example gas or a nutrient medium, can be supplied to the cells or tissue cultures situated in the well, by way of these ports. Control devices can be present for guiding fluids, for example gases or nutrient media, into the wells, and used fluids out of the wells.

The aforementioned apparatuses also represent special solutions that are not easily compatible with the usual standard equipment of a laboratory, particularly with multiwell plates, in the wells of which culture vessels are suspended, and therefore cannot be integrated into the established work sequences in all-embracing and therefore time-saving and cost-saving manner.

Proceeding from this state of the art, the invention is based on the task of making available an exposure apparatus for carrying out in vitro experiments with technical replicates of at least one biological test system, to which replicates an exposure medium can be applied by perfusion, forming an exposure atmosphere, which apparatus forms an alternative to the said special solutions, which are not easily compatible with the usual standard equipment of a laboratory and therefore cannot be integrated into the established work sequences in time-saving and cost-saving manner. Furthermore, the corresponding exposure apparatus is supposed to ensure great reproducibility and effectiveness of functionality, which is particularly supposed to allow individual application to the biological test systems. Beyond that, a corresponding exposure apparatus is supposed to be made available, in which mixing of fluid phases, particularly of maintenance medium and exposure medium, is prevented.

This task is accomplished by means of an exposure apparatus having the characteristics of claim 1. Further developments and advantageous embodiments of the invention are evident from the dependent claims.

The exposure apparatus according to the invention, for carrying out in vitro experiments with technical replicates of at least one biological test system, to which replicates an exposure medium can be applied by perfusion, forming an exposure atmosphere on or above the biological test system, comprises an exposure cap, which is dimensioned in such a manner that it can be set onto a standard multiwell plate and connected with the latter by means of suitable connection elements, wherein the exposure cap has multiple line elements, each having at least one feed line and at least one discharge line for an exposure medium, and each line element is assigned to a specific well of the standard multiwell plate, preferably one provided with a biological test system, to form the exposure atmosphere within the specific well, wherein the exposure cap can be set onto the standard multiwell plate and connected with it, in such, a manner that the exposure atmosphere that forms within each specific well during the in vitro experiment is tightly closed off relative to the ambient atmosphere and any maintenance medium that might be present, wherein exposure medium can be supplied and discharged only by way of the line element that is assigned to it, in each instance.

For the first time, in vitro experiments with technical replicates of at least one biological test system, to which replicates an exposure medium can be applied by perfusion, forming an exposure atmosphere on or above the biological test system, are possible with the exposure apparatus according to the invention, using standard multiwell plates, which possess a number of wells that are standardized in terms of positioning and dimensioning, which wells are also referred to as depressions or cavities, and thereby make it possible to carry out a great number of studies, at high quality standards, in part in automated manner, with a working method that saves time and costs. The exposure apparatus according to the invention is therefore compatible with the usual standard equipment of a laboratory, and can be integrated into the established work sequences, in time-saving and cost-saving manner. The exposure apparatus according to the invention ensures great reproducibility and effectiveness of functionality, particularly due to the formation of the closed exposure atmosphere within the specific wells; this particularly allows individual application to the biological test systems. Furthermore, in this way mixing of fluid phases, particularly of maintenance medium and exposure medium, is reliably prevented.

Standard multiwell plates are known as standard sample vessels in the sector of cell and tissue culture technology. They serve for accommodation and study of the most varied biological test systems.

The standard multiwell plates are disposable mass-produced products, common in the laboratory, which allow high throughput of biological test systems.

Typically, such standard multiwell plates are configured to be rectangular, and are produced from plastic, for example polystyrene, polypropylene, polycarbonate or polyethylene.

In this regard, individual wells, also referred to as depressions or cavities, are disposed on such a plate to accommodate the biological test systems, essentially in the form of a matrix. The wells can be accommodations that are already integrated into the standard multiwell plate, or ones that are accommodated in integrated wells that are present or in correspondingly disposed recesses of the standard multiwell plate as separate culture vessels, called inserts.

Multiwell plates having the configuration of 6 wells, 12 wells, 24 wells, 48 wells or 96 wells are preferably suitable for the exposure apparatus according to the invention.

Suitable standard multiwell plates are offered for sale and distributed by a number of commercial manufacturers, for example by Corning Inc., BD Biosciences, Biochrom AG, Greiner GmbH or Nunc GmbH & Co. KG.

Standard multiwell plates are also referred to as standardized PCR (polymerase chain reaction) plates, microtiter plates or HTS (high throughput screening) microliter plates.

Generally recognized standardization of the dimensions and the structure of a standard multiwell plate is published by the Society for Laboratory Automation and Screening (SLAS), a society of scientists and engineers associated with the American National Standards Institute (ANSI), in the standards (http://www.slas.org/education/microplate.cfm):

ANSI/SLAS 1-2004: Microplates—Footprint Dimensions
ANSI/SLAS 2-2004: Microplates—Height Dimensions
ANSI/SLAS 3-2004: Microplates—Bottom Outside Flange Dimensions
ANSI/SLAS 4-2004: Microplates—Well Positions
ANSI/SLAS 6-2012: Microplates—Well Bottom Elevation.

It can be advantageous if one or more than one sealing means is provided between exposure cap and standard multiwell plate, to close the exposure atmosphere off tightly.

It can be advantageous if the sealing means is a seal that runs circumferentially around the respective well or the opening of the respective well and/or a seal that runs circumferentially around the respective line element.

It can be advantageous if the sealing means is a sealing mat that can be affixed or has been affixed to the standard multiwell plate and/or a sealing mat that can be affixed or has been affixed to the side of the exposure cap that faces toward the standard multiwell plate, with corresponding recesses for the specific wells or openings of the specific wells and/or with corresponding recesses for the line elements assigned to the specific wells.

It can be practical if the line element assigned to a specific well of the standard multiwell plate, in each instance, projects out of the side of the exposure cap that faces toward the standard multiwell plate. It is advantageous if the line element is configured in tubular shape, particularly has an essentially tubular feed line for the exposure medium and an essentially tubular discharge line for the exposure medium. In order to achieve uniform and effective exposure of the biological test system contained in a specific well, it can be advantageous if the feed line can be brought closer to the biological test system than the discharge line, in other words the feed line projects farther out of the side of the exposure cap that faces toward the standard multiwell plate than the discharge line does. It can be particularly advantageous if the line element is configured, in space-saving manner, in such a manner that the feed line is disposed at least partially within the discharge line, and projects out of the latter in the direction of the well. In this regard, feed line and discharge line can be configured concentrically, at least in part. It is advantageous if flow guidance therefore takes place according to the pipe-in-pipe principle, in corresponding coaxial manner, in counter-current, at least in part. It can be advantageous if the feed line widens in its end region facing the biological test system, particularly widens conically.

It can be advantageous if the line element can be introduced into the well in such a manner, when the exposure cap is set onto the standard multiwell plate and/or afterward, in such a manner that a sealing means provided on the outside of the line element and surrounding it tightly closes off the line element relative to the inner wall of the well, to form the closed-off exposure atmosphere. The circumferential sealing means therefore does not lie on the edges of the well. If the line element is configured, in space-saving manner, in such a manner that the feed line is disposed within the discharge line, at least in part, and projects out of the latter in the direction of the well, the circumferential sealing means is a sealing means provided on the outside of the discharge line and surrounding the latter. Because the wells usually have a round cross-section, it can be advantageous if the sealing means also has a circular circumference. Furthermore, it can be advantageous, when introducing the line element into and pulling it out of the well, if the sealing means is configured to be flexible, at least in its end region that faces toward the inner wall of the well. This can take place by means of a corresponding material selection and/or in that the sealing means becomes thinner toward the inner wall of the well, in other words the material thickness of the sealing means decreases in the direction of the inner wall of the well, proceeding from the line element. As a result, the sealing means can also be designed universally for wells having different dimensions, to a certain extent.

It can be advantageous if a multiwell plate that is compatible with the multiwell plate standard can be used in place of the standard multiwell plate. Such a plate, which is compatible in terms of its format and in terms of the placement and number of its wells, is disclosed in DE 10 2007 030 413 A1, for example, the disclosure content of which is hereby explicitly incorporated into the disclosure content of the present patent application, by reference.

It can be practical if the connection elements are such that the exposure cap can be reversibly clamped in place on the standard multiwell plate.

It can be advantageous if the connection elements comprise locking elements that hold the exposure cap and the standard multiwell plate together, preferably under tension.

It can be practical if the connection elements are such that the standard multiwell plate and preferably the specific wells are fixed in place while the experiment is being carried out.

It can be advantageous if the connection elements are clamping jaws disposed on the exposure cap.

It can be advantageous if the exposure cap has a cap holder frame that can be set onto the standard multiwell plate and can be connected with the latter by means of the connection elements.

It can be practical if the cap holder frame sheathes the standard multiwell plate, at least in part.

It can be practical if the exposure cap has a movable cap head, which interacts with the line elements, wherein the line element assigned to a specific well, in each instance, can be moved into the specific well after the exposure cap has been set onto the standard multiwell plats, by moving the cap head in the direction of the standard multiwell plate.

It can be advantageous if the cap head is disposed on the cap holder frame and connected with the latter, wherein the cap head can be locked into the cap holder frame, by moving the cap head in the direction of the cap holder frame, by means of locking and unlocking elements preferably disposed on the cap head, for the purpose of carrying out the experiment or while it is being carried out, in such a manner that the line elements are fixed in place, wherein the locking elements hold the cap head and the cap holder frame together, preferably under tension.

It can be advantageous if, after the experiment has been carried out, the cap head can be unlocked from the cap holder frame by means of the looking and unlocking elements, in such a manner that the line elements can be released from the wells by moving the cap head in the opposite direction from the previous one. If the wells are accommodations that are accommodated or suspended in existing integrated wells or in correspondingly disposed recesses of the standard multiwell plates, as separate culture vessels, called inserts, the cap holder frame holds the insert back or down in the case of a corresponding unlocking movement of the cap head. As a result, only then can the line elements be moved out of the culture vessels or inserts in the first place, when the cap head is moved. Otherwise, the inserts would lift out of the multiwell plate with the unlocking movement of the cap head, in disadvantageous manner. In this regard, holding can take place directly or indirectly, for example by way of a sealing means disposed in or on the cap holder frame.

It can be advantageous if, in order to carry out the experiment, the cap holder frame can first be locked into the standard multiwell plate, and subsequently the cap head is locked into the cap holder frame, and that after the experiment has been carried out, the cap head can be unlocked from the cap holder frame, and subsequently the cap holder frame can be unlocked from the standard multiwell plate.

It can be practical if the exposure apparatus has a base accommodation for accommodating the standard multiwell plate.

It can be advantageous if the base accommodation sheathes the standard multiwell plate, at least in part.

It can be advantageous if the exposure cap, particularly the cap holder frame of the exposure cap, can be positioned and set onto the base accommodation by means of at least one positioning aid.

It can be advantageous if the positioning aid has a pin disposed on the base accommodation and a recess in the exposure cap, provided to correspond to this pin, particularly in the cap holder frame of the exposure cap.

It can be advantageous if, after locking, the standard multiwell plate accommodated in the base accommodation is completely sheathed by the base accommodation and the exposure cap set onto the standard multiwell plate and the base accommodation, or the cap holder frame of the exposure cap.

It can be advantageous if the exposure medium that can be conducted through the line elements is liquid or gaseous, wherein the exposure medium can be provided with or without a test substance.

It can be advantageous if a sealing means that surrounds the line element is provided between cap holder frame and cap head.

It can be advantageous if the exposure cap, the cap head, the cap holder frame and/or the base accommodation can be tempered, entirely or in part, each on its own or together, at least in part, particularly can be heated electrically, preferably in such a manner that a thermal gradient forms within the exposure apparatus, which gradient can particularly be used for targeted deposition of substances from an aerosol stream, by means of thermophoresis. The use of Peltier elements is particularly advantageous for the formation of a temperature gradient.

As the result of the targeted tempering of the parts or components mentioned above, a temperature gradient exists in the aerosol stream, thereby causing a force to act on the particles contained in the aerosol stream, in the direction of the lower temperature. In this way, particles can be conducted to the biological test system in targeted manner. It can be advantageous, in order to set a temperature gradient, if the exposure cap, the cap head, the cap holder frame and/or the base accommodation are insulated relative to one another, in whole or in part, preferably by insulation means. Preferably, sealing means that are present can also be configured as insulation means for this purpose.

It can be advantageous if the bottom of at least one well of the standard multiwell plate is configured as a permeable carrier or has such a carrier, if applicable also in addition, wherein the biological test system is disposed on this carrier.

Preferably, the permeable carrier is configured in such a manner that on the one hand, it is suitable for accommodation of the biological test system, and on the other hand, allows physical separation of the liquid or gaseous phase that forms the exposure atmosphere from the liquid phase that forms the maintenance medium. Consequently, the pore size and pore density of the permeable carrier can vary as a function of the type of biological testing system and the type as well as viscosity of the maintenance medium.

Preferably, the permeable carrier can be a microporous membrane. To accommodate the biological test system, the well can also be structured by means of a commercially available insert, called a cell culture insert, which can be introduced into the multiwell plate, wherein the permeable carrier forms the bottom membrane of the well.

It can be advantageous if at least one feed line and discharge line system, is provided, which is connected or can be connected with one or more than one line element for feed and discharge, for perfusive exposure of the technical replicates of at least one biological test system.

The feed line system comprises ail the apparatuses that are suitable for conducting the liquid or gaseous exposure medium over the surface of the biological test system, to form an exposure atmosphere above the biological test system.

The feed line system can also comprise all the apparatuses that implement bringing the liquid or gaseous exposure medium up by means of their design, in particular manner, for example having a hyperbolic inner profile for targeted deposition of aerosol droplets.

Furthermore, the feed line system can preferably also have apparatuses for electrostatic deposition of particles or droplets and/or a charging apparatus. Such apparatuses are known, for example, from DE 195 26 533 A1. The disclosure of this patent application is hereby also incorporated into the present application, with its full content, by reference.

It can be practical if a division of the exposure medium among the technical replicates or among the specific wells is provided, by means of the line elements assigned to these wells, wherein the division can be carried out, in particular, in linear, radial, horizontal and/or vertical manner.

It can be advantageous if the division can be carried out from different exposure media.

It can be advantageous if the feed line or the feed line system stands in connection with at least one device that treats the exposure medium, preferably a device for thermostatization of the exposure medium, and/or a device that detects the exposure medium.

It can be practical if the feed line and/or discharge line and/or the feed line system and/or discharge line system of the respective line element are configured in such a manner that the exposure medium is conducted or conveyed through the well or over the biological test system in controlled manner, preferably by means of a partial vacuum applied to the discharge line or discharge line system.

It can be advantageous if the discharge line or the discharge line system, is provided with at least one connector for an apparatus that produces a partial vacuum, particularly a pump, for example a peristaltic pump for liquid media or a membrane pump for gaseous media.

It can be advantageous if the feed line and/or discharge line or the feed line system and/or discharge line system of the exposure apparatus, particularly of the exposure cap, can be connected or are connected with control elements for uniform distribution of the exposure medium to specific wells, or contain these elements. The control elements can be, for example, mass flow controllers as well as constructive apparatuses for flow modulation and/or valves.

It can be advantageous if the exposure apparatus has one or more than one module or can be connected with the latter, in such a manner that the exposure medium/media to be fed in and/or discharged can be subjected to physical/chemical or biological treatment. This can be, for example, humidification, $CO_2$ enrichment, electrostatic charging or neutralization, spiking with reference particles or gases, injection of biologically active components such as antibodies, pollen, etc, and/or thermostatization.

It can be advantageous if the treatment of the exposure medium can be carried out in the same manner for all technical replicates or all specific wells, or differently for individual ones of the specific wells.

It can be practical if multiple treatment methods can be used in combination in a module, or only individually.

It can be advantageous if the at least one module for treatment is disposed ahead of and/or after at least one module for detection of the exposure medium/media to be fed in and/or discharged.

It can be advantageous if the exposure apparatus has one or more than one module or can be connected with the latter, in such a manner that the exposure medium/media to be fed in and/or discharged and/or the biological test system can be subjected to physical/chemical or biological analysis. The analysis methods can be, for example, scattered light measurement, ph determination, spectroscopic analysis methods or antibody-based analysis methods.

It can be practical if the analysis of the exposure medium can be carried out in the same manner for all technical replicates or all specific wells, or differently for individual ones of the technical replicates or the specific wells.

It can be practical if multiple analysis methods can be used in a module, in combination or only individually.

It can be advantageous if the at least one module for analysis is disposed ahead of and/or after at least one module for treatment of the exposure medium/media to be fed in and/or discharged.

It can be advantageous if a module for physical/chemical or biological analysis can be carried out within or underneath the standard multiwell plate.

It can be practical if at least one well, a group of wells, or each well of a group stands in connection with a feed system and discharge system, by way of the line element assigned to a well, in each instance, composed of a feed line and discharge line, in such a manner that each well, each group of wells or each well of a group, individually, has an exposure medium with or without test substance flowing through it, at the same or different exposure volume streams.

It can be advantageous if at least one further volume stream is provided, aside from the exposure volume stream conducted into the well and out of the well, in each instance, by way of the line element, by way of which further stream the exposure medium can be conducted through the exposure apparatus in the manner of pre-conveying, wherein exposure volume streams that can be predetermined can be conducted or fed out of this further volume stream.

It can be advantageous if the at least one further volume stream can be operated in the manner of pre-conveying, at a different volume flow rate, preferably a greater volume flow rate than the sum of the individual exposure volume streams.

It can be advantageous if multiple further volume streams are provided, wherein exposure volume streams that can be predetermined can be brought into connection with each of the further volume streams.

It can be practical if one or more than one well of the standard multiwell plate has no line element assigned to it, wherein the well or this group of wells can be carried along in the in vitro experiment as what is called a control sample.

It can be advantageous if one or more than one well has a line element assigned to it, in each instance, by means of which the exposure medium without test substance can be conducted to the well or this group of wells, and can be carried along in the in vitro experiment as what is called a blind sample.

It can be advantageous if one or more than one well has a line element assigned to it, in each instance, by means of which the exposure medium with test substance can be conducted to the well or this group of wells, and can be carried along in the in vitro experiment as the actual sample.

If can be advantageous if a maintenance medium can be supplied to or is assigned to the standard multiwell plate, which medium stands in direct contact with the underside of the well or of the permeable carrier, on which the biological test system is disposed, to supply the biological test system.

It can be practical if the exposure apparatus has one or more than one module or can be connected with the latter, in order to subject the maintenance medium or the maintenance medium/media that is/are fed in and/or discharged to physical/chemical or biological treatment. The treatment can be, for example, the addition of biologically active substances, the addition of metabolizing proteins, the addition of acid/base for pH regulation, or thermostatization.

It can be practical if treatment of the maintenance medium can be carried out in the same manner for ail technical replicates or for all specific wells, or differently for individual ones of the technical replicates or of the specific wells.

It can be advantageous if multiple treatment methods can be used in a module, in combination or only individually.

It can be practical if the at least one module for treatment is disposed ahead of and/or after at least one module for detection of the maintenance medium or of the maintenance medium/media to be fed in and/or discharged.

It can be advantageous if the exposure apparatus has one or more than one module or can be connected with the latter, in such a manner that the maintenance medium or the maintenance medium/media to be fed in and/or discharged can be subjected to a physical/chemical or biological analysis. In this regard, this can be a scattered light measurement, a pH determination, spectroscopic analysis methods or antibody-based analysis methods.

It can be advantageous if the analysis of the maintenance medium can be carried out in the same manner for all technical replicates or for all specific wells, or differently for individual ones of the technical replicates or specific wells.

It can be advantageous if the at least one module for analysis is disposed ahead of and/or after at least one module for treatment of the maintenance medium or of the exposure medium/media to be fed in and/or discharged.

It can be advantageous if a module for physical/chemical or biological analysis can be carried out within or underneath the standard multiwell plate.

In the following, the invention will be explained using exemplary embodiments that are shown in the drawing. The drawing shows:

FIG. 1 schematically, in cross-section, an exposure apparatus according to the invention, with a multiwell plate in the open position.

Figure 2:
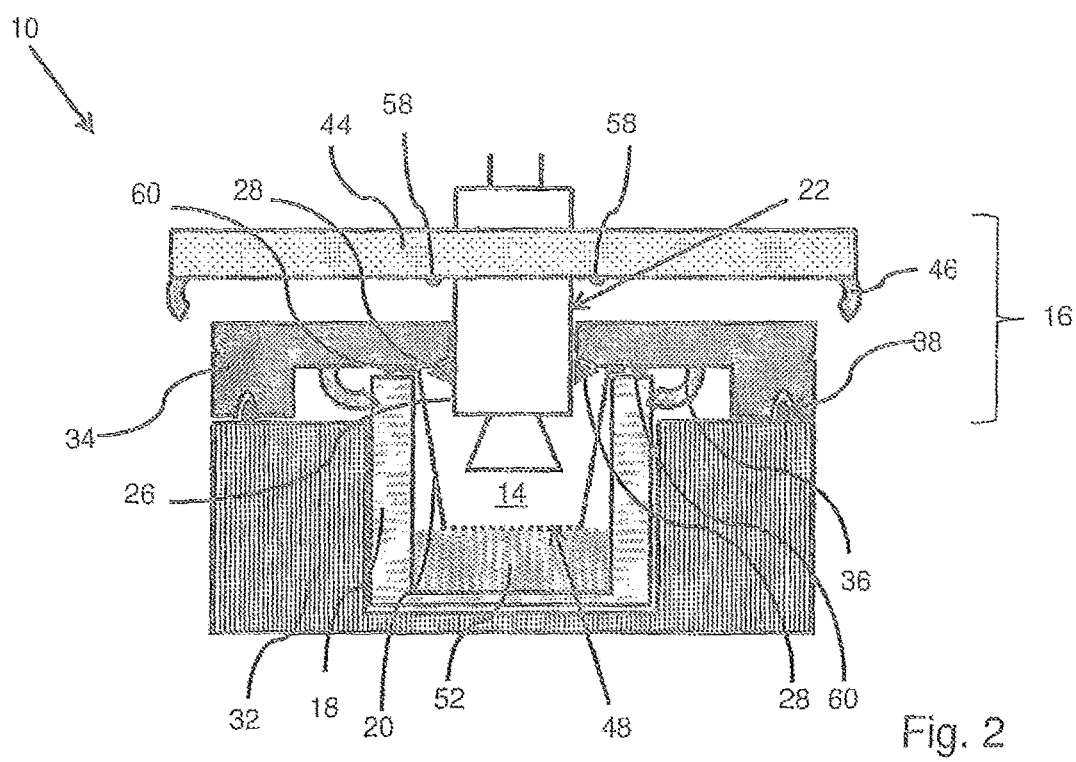
Figure 3:
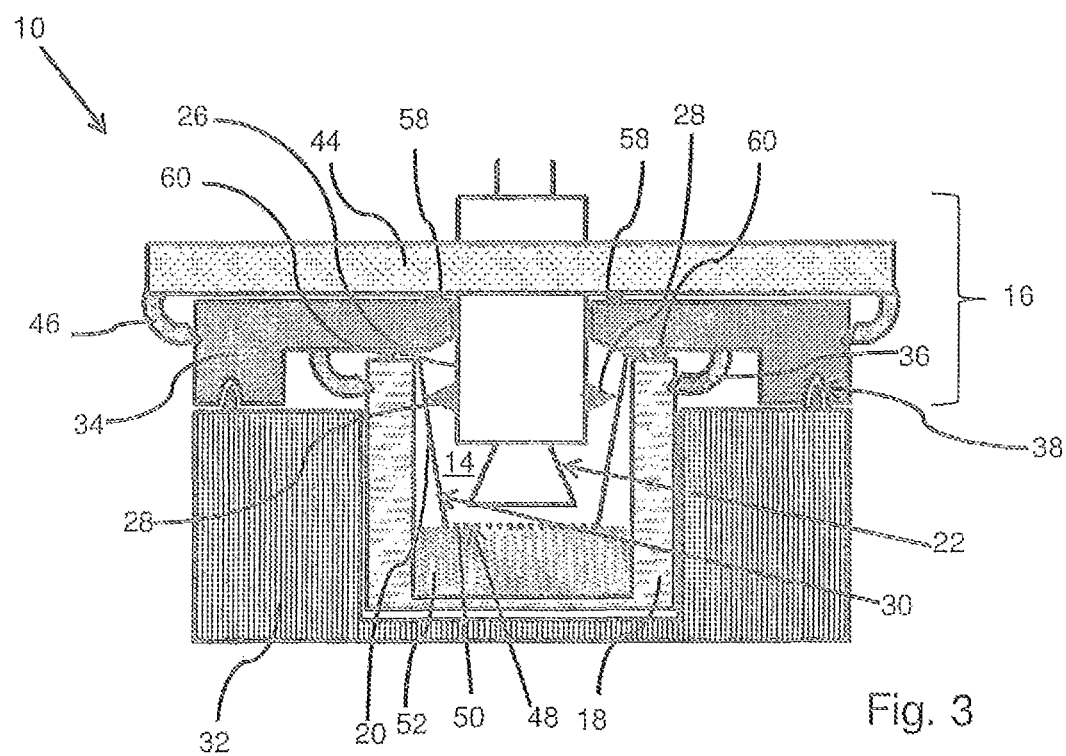

FIG. 2 schematically, in cross-section, the exposure apparatus according to the invention from FIG. 1, with the multiwell plate in a first locked position, FIG. 3 schematically, in cross-section, the exposure apparatus according to the invention from FIG. 1, with the multiwell plate in a second locked position.

Figure 4:
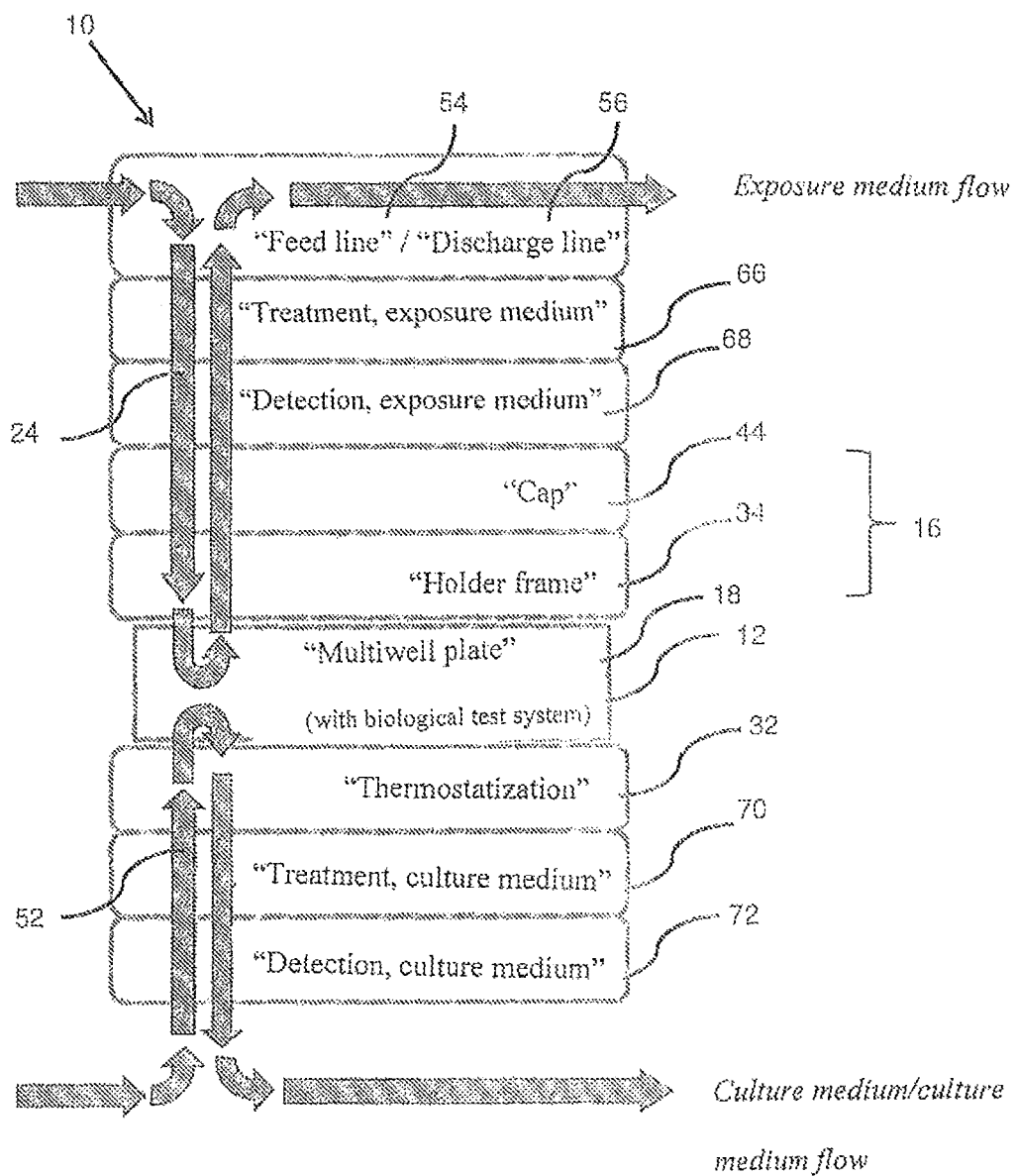
Figure 5:
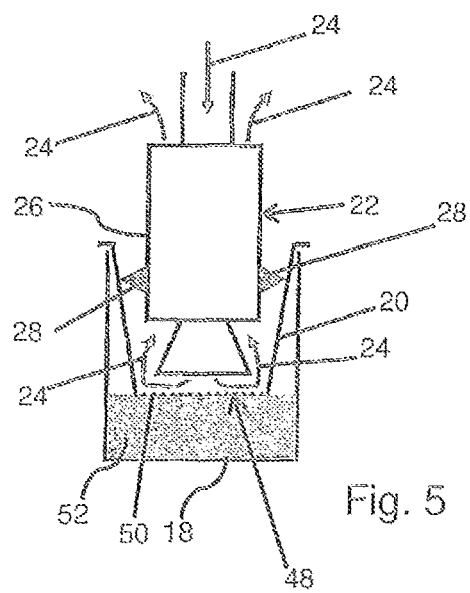
Figure 6:
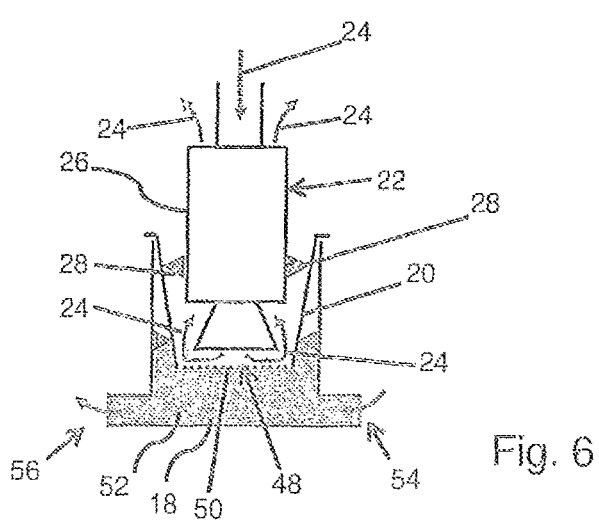
Figure 7:
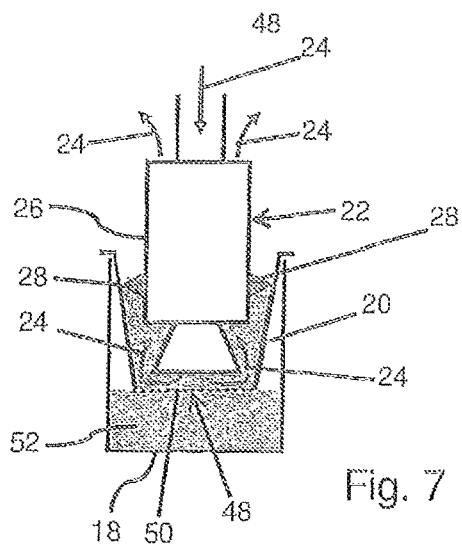
Figure 8:
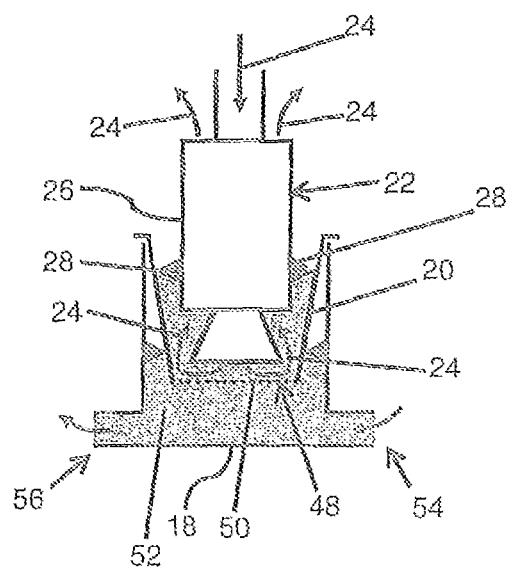

FIG. 4 a schematic representation regarding the function of the exposure apparatus according to the invention, during an experiment, FIG. 5 a first exemplary use or exemplary embodiment of the exposure apparatus according to the invention, FIG. 6 a second exemplary use or exemplary embodiment of the exposure apparatus according to the invention, FIG. 7 a third exemplary use or exemplary embodiment of the exposure apparatus according to the invention, FIG. 8 a fourth exemplary use or exemplary embodiment of the exposure apparatus according to the invention.

Figure 9:
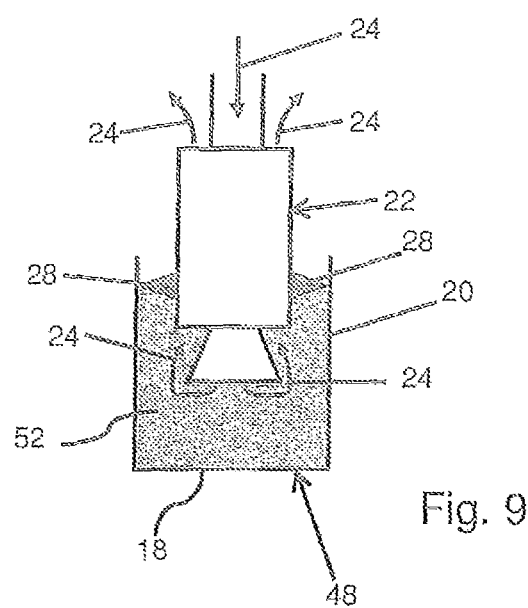
Figure 10:
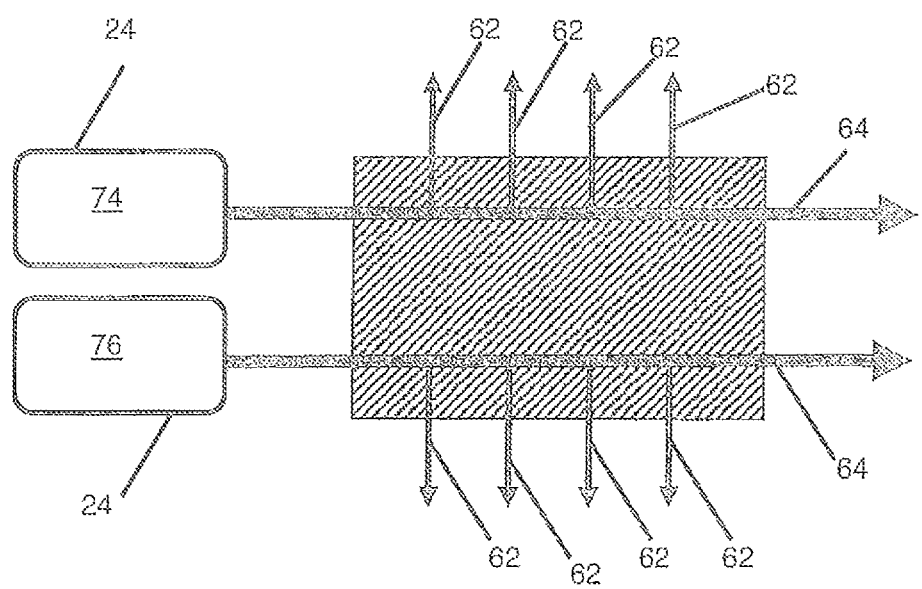

FIG. 9 a fifth exemplary use or exemplary embodiment of the exposure apparatus according to the invention, and FIG. 10 schematically, a possible division of the exposure medium among technical replicates that are assigned to biological test systems, in each instance.

When the same reference numbers are used in FIGS. 1 to 10, these refer to the same parts or components, so that for the purpose of avoiding repetition, parts or components that have already been described do not have to be discussed again for every figure description.

FIG. 1 to 3 schematically show an exposure apparatus 10 according to the invention, in cross-section, having a multiwell plate 18 in the open position (FIG. 1), in a first locked position (FIG. 2), and in a second locked position (FIG. 3). The multiwell plate 18 is a standard multiwell plate, wherein for the sake of clarity, only one well 20 of the standard multiwell plate 18 is shown.

The exposure apparatus 10 that is shown serves to carry out in vitro experiments with technical replicates of at least one biological test system 12. In this regard, the technical replicates, with their corresponding biological test systems have an exposure medium 24 applied to them by perfusion, forming an exposure atmosphere 14.

The exposure cap 16 is dimensioned in such a manner that it can toe set onto the standard multiwell plate 18 and firmly connected and locked into the latter 18 by means of suitable connection elements, in the present case by means of locking elements 36, for example in the form of clamping jaws.

The exposure cap 16 has multiple line elements 22, each having at least one feed line 54 and at least one discharge line 56 for an exposure medium 24, wherein each line element 22 is assigned to a specific well 20, preferably provided with a biological test system 12, of the standard multiwell plate 18, to form the exposure atmosphere 14 within the specific well 20.

The exposure cap 16 can be set onto the standard multiwell plate 18 and can be connected with or locked into the latter, in such a manner that the exposure atmosphere 14 that forms within the specific well 20 during the in vitro experiment is tightly closed off. When this happens, exposure medium 14 can be only be fed to the specific well 20 and discharged from it by way of the line element 22 assigned to it, in each instance.

One or more than one sealing means 23, 60 is provided between exposure cap 16 and standard multiwell plate IS, in order to tightly close off the exposure atmosphere 14.

The sealing means 28, 60 is a seal that runs circumferentially around the respective well 20 or the opening of the respective well 20 and/or the respective line element 22.

The sealing means 60 is a sealing mat affixed on the side of the exposure cap 16 that faces toward the standard multiwell plate 18, with corresponding recesses for the specific wells 20 or openings of the specific wells 20 and/or with corresponding recesses for the line elements 22 assigned to the specific wells 20. Such a sealing means 60 can be sufficient for forming a closed-off exposure atmosphere 14, if the specific well 20 does not have any lateral openings present at the top edge of the well, which leave a connection to the maintenance medium open. These sealing means 60 can be sufficient if the well 20 follows the base plate of the standard multiwell plate 18 continuously over its circumference. Usually, such a sealing means is not sufficient if the well 20—as in the present case—can be suspended in the standard multiwell plate 18 as what is called an insert.

For this purpose, it is provided that the line element 22 assigned to a specific well 20 of the standard multiwell plate 18, in each instance, projects out of the side of the exposure cap 16 that faces toward the standard multiwell plate 18.

In this regard, the line element 22 is introduced into the well 20 when the exposure cap 16 is set onto the standard multiwell plate 18 and/or afterward, in such a manner that a sealing means 28 provided on the outside 26 of the line element 22 and surrounding it circumferentially tightly closes off the line element 22 relative to the inner wall 30 of the well 20, to form the closed-off exposure atmosphere 14.

The present exposure cap 16 has a cap holder frame 34 that can be set onto the standard multiwell plate 18 and can be connected with the latter by means of the connection elements or locking elements 36. After having been set on, the cap holder frame 34 partially sheathes the standard multiwell plate 18, as can be recognized well in FIG. 3.

The exposure cap 16 furthermore has a movable cap head 44 that interacts with the line elements 22, wherein the line element 22 assigned to a specific well 20, in each instance, can be moved into the specific well 20 by means of moving the cap head 44 in the direction of the standard multiwell plate 18 after the exposure cap 16 has been set onto the standard multiwell plate 18. In this regard, the cap head 44 is disposed on the cap holder frame 34 and connected with the latter, wherein the cap head 14 can be locked into the cap holder frame 34, by means of locking and unlocking elements 46 preferably disposed on the cap head 44, by means of moving the cap head 44 in the direction of the cap holder frame 34, in order to carry out the experiment or while it is being carried out, in such a manner that the line elements 22 are fixed in place, wherein the locking elements 46 the cap head 44 and the cap holder frame 34 together, preferably under tension.

After the experiment has been carried out, the cap head 44 can also be unlocked from the cap holder frame 34 again, by means of the locking and unlocking elements 46, in such a manner that the line elements 22 can be released from the wells 20 by moving the cap head 44 in the opposite direction from the previous one; this is not shown here. If—as shown in FIG. 1 to 3—culture vessels or what are called inserts 20 are suspended in the cavities of the standard multiwell plate 18, the aforementioned two-step unlocking allows safe removal of the respective line element 22 from the insert 20, because the insert 20 is held back or down by the cap holder frame 34 after a corresponding unlocking movement of the cap head 48. Otherwise, the insert 20 disadvantageously be lifted out of the multiwell plate 18 the unlocking movement of the cap head 48. The insert 20 then therefore no longer be positioned in the multiwell plate 18 for further use, for example analysis.

To carry out the experiment, the cap holder frame 34 can therefore first be locked into the standard multiwell plate 18, and subsequently the cap head 44 can be locked into the cap holder frame 34. After the experiment has been carried out, first the cap head 44 can be unlocked from the cap holder frame 34, and subsequently, the cap holder frame 34 can be unlocked from the standard multiwell plate 13.

The exposure apparatus 10 according to the invention has a base accommodation 32 for accommodation of the standard multiwell plate 18, virtually as a further module. In this regard, the cap holder frame 34 of the exposure cap 16 can be positioned and set onto the base accommodation 32 by means of at least one positioning aid 38. The positioning aid 38 has multiple pins 40 on the base accommodation 32, and a recess 42 in the cap holder frame 34 of the exposure cap 16 provided accordingly for each pin 40, in each instance.

As can be recognized well in FIG. 3, the standard multiwell plate 18 is partially sheathed by the base accommodation 32, wherein in the assembled state of exposure cap 16 and base accommodation 32, the standard multiwell plate 18 is completely sheathed.

A further sealing means 58 that runs circumferentially around the line element. 22 is provided between cap holder frame 34 and cap head 44.

It is advantageous if the cap head 44, the cap holder frame 34, and the base accommodation 32 can be tempered, particularly heated electrically, preferably in such a manner that a thermal gradient forms within the assembled exposure apparatus 10—as shown in FIG. 3—which gradient can particularly be used for targeted deposition of test substances from an aerosol stream as the exposure medium 24, by means of thermophoresis.

In FIG. 1 to 3, it can be recognized well that the bottom 48 of a well 20 of the standard multiwell plate 18 is configured as a permeable carrier 50 or has such a carrier 50, wherein the biological test system 12 is disposed or cultured on the latter.

The standard multiwell plate 18 can have a maintenance medium 52 assigned to it, which stands in direct contact with the underside of the well 20 or of the permeable carrier 50, on which well or carrier the biological test system is disposed, in order to supply the biological test system 12.

FIG. 4 shows a schematic representation regarding the function of the exposure apparatus 10 according to the invention during an experiment. Different functional modules are shown, which are assigned to the exposure apparatus 10 according to the invention. Furthermore, the flow of the exposure medium 24 and of the maintenance or culture medium 52 is shown, in connection with the individual functional modules, in each instance, wherein the culture medium 52 is assigned to the respective biological test system predominantly in static manner, in other words not in flowing manner.

The functional modules "feed line/discharge line," "cap" or cap head 44, "holder frame" or cap holder frame 34, "multiwell plate" or standard multiwell plate 18 with the biological test system, as well as "thermostatization" or base accommodation 32 can be tempered have already been discussed.

It is advantageous that the feed line 54 and/or discharge line 56 can stand in connection with at least one device 66 that treats the exposure medium 24, as at least one further module, for example a module for thermostatization of the exposure medium 24. It is advantageous that the feed line 54 and/or discharge line 56 can stand in connection with at least one device 68 that detects the exposure medium 24, as at least one further module.

The feed line and/or discharge line 54, 56 and/or feed line system and/or discharge line system of the respective line element 22 are configured in such a manner that the exposure medium 24 is conducted or conveyed through the well 20 or over the biological test system in controlled manner, preferably by means of a partial vacuum that is applied to the discharge line 56 or the discharge line system.

The discharge line 56 or the discharge line system is provided with at least one connector for an apparatus that produces a partial vacuum, particularly a peristaltic pump for liquid media or a membrane pump for gaseous media.

It is advantageous that the feed line and/or discharge line 54, or the feed line system and/or discharge line system of the exposure apparatus 10, particularly of the exposure cap 16, can be connected or is connected with control elements, not shown here, for uniform distribution of the exposure medium 24 among specific wells 20 of the standard multiwell plate 18. The control elements can be, for example, mass flow controllers as well as constructive apparatuses for flow modulation and/or valves.

It is advantageous if the exposure apparatus 10 has one or more than one module or can be connected with the latter, in such a manner that the exposure medium/media to be fed in and/or discharged can be subjected to a physical/chemical or biological treatment. This can be, for example, humidification, $CO_2$ enrichment, electrostatic charging or neutralization, spiking with reference particles or gases, injection of biologically active components such as antibodies, pollen, etc, and/or thermostatization.

The treatment 66 of the exposure medium 24 can be carried out in the same manner for all technical replicates or all specific wells 20, or differently for individual ones of the technical replicates or of the specific wells 20. In this way, test groups and control groups can be formed.

Multiple treatment methods can be used in combination in a module, or only individually.

The at least one module for treatment can be disposed ahead of and/or after at least one module described below, for detection of the exposure medium/media to be fed in and/or discharged.

The exposure apparatus 10 according to the invention has one or more than one module 68 or can be connected with the latter, in such a manner that the exposure medium/media to be fed in and/or discharged and/or the biological test system, can be subjected to a physical/chemical, or biological analysis. The analysis methods can be, for example, a scattered light measurement, a pH determination, spectroscopic analysis methods or antibody-based analysis methods.

The analysis of the exposure medium 24 can be carried out in the same manner for ail technical replicates or all specific wells 20, or differently for individual ones of the technical replicates or the specific wells 20.

Multiple analysis methods can be used in combination in a module, or only individually.

For analysis, at least one module is disposed ahead of and/or at least one module described above, for treatment of the exposure medium/media to be fed in and/or discharged.

It is advantageous that a module for physical/chemical or biological analysis can be carried out within or underneath the standard multiwell plate 18.

As has already been explained, a maintenance medium 52 can be supplied to or is assigned to the standard multiwell plate 18, which medium stands in direct contact with the underside of the well 20 or of the permeable carrier 50 on which well or carrier the biological test system is disposed, to supply the biological test system.

It is advantageous if the exposure apparatus 10 according to the invention has one or more than one module or can be connected with the latter, in order to subject the maintenance medium 52 the maintenance medium/media 52 that is/are fed in and/or discharged to a physical/chemical or biological treatment. The treatment can be, for example, the addition of biologically active substances, the addition of metabolizing proteins, the addition of acid/base for pH regulation, or thermostatization.

The treatment of the maintenance medium 52 can be carried out in the same manner for all technical replicates or for all specific wells 20, or differently for individual ones of the technical replicates or the specific wells 20. In this way, control groups and test groups can be formed.

Multiple treatment methods can be used in combination in a module, or only individually.

At least one module 70 for treatment is disposed ahead of and/or after at least one module 72 described below, for detection of the maintenance medium 52 or of the maintenance medium/media 52 be fed in and/or discharged.

The exposure apparatus 10 according to the invention has one or more than one module 72 or can be connected with the latter, in such a manner that the maintenance medium 52 or the maintenance medium/media 52 to be fed in and/or discharged can be subjected to a physical/chemical or biological analysis. In this regard, this can be a scattered light measurement, ph determination, spectroscopic analysis methods or antibody-based analysis methods.

The analysis of the maintenance medium 52 can be carried out in the same manner for all technical replicates or for all specific wells 20, or differently for individual ones of the technical replicates or of the specific wells 20. In this way, control groups and test groups can be formed, for example.

The at least one module 72 for analysis can be disposed ahead of and/or after at least one module 70 described above for treatment of the maintenance medium 52 or of the exposure medium/media 24 to be fed in and/or discharged.

A module 72 can be carried out within or underneath the standard multiwell plate 18, for physical/chemical or biological analysis.

A direct analysis of the biological, test system 12 in the standard multiwell plate 18 can also be provided, for example by means of fluorescence-spectroscopy methods.

FIG. 5 to 9 show five different exemplary uses or exemplary embodiments of the exposure apparatus according to the invention in connection with a standard multiwell plate (FIGS. 5, 7, and 9) or of an exposure apparatus that is compatible with a standard multiwell plate (FIGS. 6 and 8). The exposure apparatus last mentioned is disclosed in DE 10 2007 030 413 A1, the disclosure content of which is hereby incorporated into the disclosure of the present patent application, by explicit reference.

The exemplary uses or exemplary embodiments differ in terms of the type of exposure medium 24 (fluid phase I: liquid/gaseous), in the manner of supplying the maintenance medium 52 (fluid phase II: perfusive/static), and—as has already been mentioned—in the type of the multiwell plate (standard multiwell plate/exposure apparatus that is compatible with standard multiwell plates, according to DE 10 2007 030 413 A1).

In a table, the exemplary uses or exemplary embodiments according to FIG. 5 to 9 can be broken down as follows:

| FIG. | Phase I | Phase II | Structure |
| --- | --- | --- | --- |
| 5 | gas/aerosol perfusive | liquid static | barrier culture (ALI) in standard multiwell plates |
| 6 | gas/aerosol perfusive | liquid perfusive | barrier culture (ALI) in an exposure apparatus compatible with multiwell plates, according to DE 10 2007 030 413 A1 |
| 7 | liquid perfusive | liquid static | barrier culture (liquid) in standard multiwell plates |
| 8 | liquid perfusive | liquid perfusive | barrier culture (liquid) in an exposure apparatus compatible with multiwell plates, according to DE 10 2007 030 413 A1 |
| 9 | liquid perfusive | | adherent, submerged in standard multiwell plates |

FIG. 10 schematically shows a possible division of the exposure medium among technical replicates, which are assigned to biological test systems, in each instance. In this regard, the division takes place from two different exposure media 24, wherein the one exposure medium consists of pure air 74 for a negative control, and the other exposure medium comprises the actual sample or test substance, for example in the form of a pharmacologically active aerosol 76.

Aside from the exposure volume streams 62 to be fed to and discharged from the technical replicates or specific wells 20, in each instance, two further volume streams 64 are provided, by way of which the one or the other exposure medium 74, 76 can be conducted through an upper part of the exposure apparatus 10 in the manner of pre-conveying, wherein in the present case, five exposure volume streams 62 can be conducted out of or supplied from these volume streams 64.

The other volume stream 64, in each instance, can be operated, in the manner of pre-conveying, at a different volume flow rate, preferably a greater volume flow rate, than the sum of the individual exposure volume streams 62 that stand in connection with this further volume stream 64.

In the present case, a line element 22, not shown here, is assigned to five technical replicates or to the corresponding wells 20, in each instance, by means of which element the exposure medium 24 without test substance, for example as pure air 74, can be conducted to this group of wells 20, and can thereby be carried along in the in vitro experiment as what is called a blind sample.

In the present case, a further line element 22, not shown here, is assigned to a further five technical replicates or to the corresponding wells 20, in each instance, by means of which element the exposure medium 24 with test substance, for example as a pharmacologically active aerosol 76, can be conducted to this group of wells 20, and can be carried along in the in vitro experiment as the actual sample.

Pre-conveying or the corresponding further volume stream 64 can be operated at a volume flow of 500 mL/min, for example, while each individual exposure volume stream 66 can be operated at a volume flow of 5 mL/min, for example.

Each exposure volume stream 64 can furthermore also be adjusted individually, at a predetermined volume flow for each well.

REFERENCE SYMBOL LIST

Is Part of the Specification 10 exposure apparatus
12 biological test system
14 exposure atmosphere
16 exposure cap
18 standard multiwell plate
20 well
22 line element
24 exposure medium
26 outside of the line element 22
28 sealing means of the line element 22
30 inner wall of the well 20
32 base accommodation
34 cap holder frame
36 locking element
38 positioning aid
40 pin
42 recess
44 cap head
46 locking element
48 bottom of the well
50 permeable carrier
52 maintenance medium
54 feed line
56 discharge line
58 sealing means between 34 and 44
60 sealing means between 16 and 18
62 exposure volume stream
64 further volume stream
66 treatment, exposure medium
68 detection, exposure medium
70 treatment, maintenance medium
72 detection, maintenance medium
74 pure air
76 pharmacologically active aerosol

The invention claimed is:

1. An exposure apparatus for carrying out in vitro experiments with technical replicates of at least one biological test system, to which replicates an exposure medium can be applied by perfusion, forming an exposure atmosphere on or above the biological test system, the exposure apparatus comprising:

a standard multiwell plate, an exposure cap, which is dimensioned in such a manner that the exposure cap can be set onto the standard multiwell plate and connected with the standard multiwell plate via a plurality of connection elements, wherein the exposure cap has multiple line elements, each having at least one feed line and at least one discharge line for an exposure medium, wherein each line element projects out of a side of the exposure cap that faces the standard multiwell plate and is assigned to a specific well of the standard multiwell plate to form the exposure atmosphere within the specific well, wherein the wells are holders that are already integrated into the standard multiwell plate, or holders that are accommodated, as separate culture vessels into existing integrated wells or into correspondingly disposed recesses of the standard multiwell plate, wherein the exposure cap has a cap holder frame that can be set onto the standard multiwell plate and connected with the standard multiwell plate via the plurality of connection elements and a movable cap head disposed on the cap holder frame and connected with the cap holder frame, wherein the line element assigned to a specific well, in each instance, can be moved into the specific well after the exposure cap has been set onto the standard multiwell plate, by moving the cap head that interacts with the line elements in a direction of the cap holder frame or the standard multiwell plate, and the line element assigned to the specific well can be introduced in such a manner that a circumferential sealing means provided on the outside of the line element and surrounding the line element seals the line element off tightly relative to an inner wall of the well, to form an exposure atmosphere that is sealed off during an in vitro experiment, within each specific well, wherein the exposure medium can be supplied and discharged only by way of the line element that is assigned to the exposure medium, in each instance, wherein the cap head can be locked into the cap holder frame via locking and unlocking elements for a purpose of carrying out the in vitro experiment or while the in vitro experiment is being carried out, in such a manner that the line elements are fixed in place, wherein the locking elements hold the cap head and the cap holder frame together, and wherein the cap head can be unlocked from the cap holder frame after the in vitro experiment has been conducted, via the locking and unlocking elements, in such a manner that the line elements, together with the circumferential sealing means, can be released from the wells as the cap head is moved in a direction opposite the direction of the cap holder frame or the standard multiwell plate.

2. The exposure apparatus according to claim 1, wherein more than one sealing means are provided between the exposure cap and the standard multiwell plate, to tightly close off the exposure atmosphere.

3. The exposure apparatus according to claim 2, wherein the sealing means is a seal that runs circumferentially around the respective well or an opening of the respective well.

4. The exposure apparatus according to claim 2, wherein the sealing means is a sealing mat that can be affixed or has been affixed to the standard multiwell plate and/or a sealing mat that can be affixed or has been affixed to a side of the exposure cap that faces toward the standard multiwell plate, with corresponding recesses for the specific wells or openings of the specific wells and/or with corresponding recesses for the line elements assigned to the specific wells.

5. The exposure apparatus according to claim 1, wherein a multiwell plate compatible with the multiwell plate standard can be used in place of the standard multiwell plate.

6. The exposure apparatus according to claim 1, wherein the connection elements are such that the exposure cap can be reversibly clamped in place on the standard multiwell plate.

7. The exposure apparatus according to claim 1, wherein the connection elements comprise locking elements, which hold the exposure cap and the standard multiwell plate together.

8. The exposure apparatus according to claim 1, wherein the connection elements are such that the standard multiwell plate is fixed in place while the experiment is being carried out.

9. The exposure apparatus according to claim 1, wherein the connection elements are clamping jaws disposed on the exposure cap.

10. The exposure apparatus according to claim 1, wherein the cap holder frame sheathes the standard multiwell plate, at least in part.

11. The exposure apparatus according to claim 1, wherein in order to carry out the experiment, a cap holder frame can first be locked into the standard multiwell plate, and subsequently the cap head can be locked into the cap holder frame, and wherein after the experiment has been carried out, the cap head can be unlocked from the cap holder frame, and subsequently the cap holder frame can be unlocked from the standard multiwell plate.

12. The exposure apparatus according to claim 11, further comprising a base accommodation for accommodation of the standard multiwell plate.

13. The exposure apparatus according to claim 12, wherein the base accommodation sheathes the standard multiwell plate, at least in part.

14. The exposure apparatus according to claim 12, wherein the exposure cap can be positioned and set onto the base accommodation by means of at least one positioning aid.

15. The exposure apparatus according to claim 14, wherein the positioning aid has a pin disposed on the base accommodation and a recess in the exposure cap, provided to correspond to this pin.

16. The exposure apparatus according to claim 12, wherein after locking, the standard multiwell plate accommodated in the base accommodation is completely sheathed by the base accommodation and the exposure cap or the cap holder frame of the exposure cap set onto the standard multiwell plate and the base accommodation.

17. The exposure apparatus according to claim 1, wherein the exposure medium that can be conducted through the line elements is liquid or gaseous, wherein the exposure medium can be provided with or without test substance.

18. The exposure apparatus according to claim 1, wherein a sealing means that runs circumferentially around the line element is provided between a cap holder frame and the cap head.

19. The exposure apparatus according to claim 1, wherein the exposure cap, a cap head, a cap holder frame and/or a base accommodation can be tempered, entirely or in part, each on its own or together, at least in part, in such a manner that a thermal gradient forms within the exposure apparatus, which gradient can be used for targeted deposition of substances from an aerosol stream, by means of thermophoresis.

20. The exposure apparatus according to claim 1, wherein a bottom of a well of the standard multiwell plate is configured as a permeable carrier or has such a carrier, wherein the biological test system is disposed on the carrier.

21. The exposure apparatus according to claim 1, wherein at least one feed line system and discharge line system are provided, which are connected or can be connected with one or more than one line element composed of a feed line and discharge line for perfusive exposure of the technical replicates of at least one biological test system.

22. The exposure apparatus according to claim 1, wherein a division of the exposure medium among the technical replicates or among the specific wells is provided, by means of the line elements assigned to these wells, wherein the division can be carried out in a linear, a radial, a horizontal and/or a vertical manner.

23. The exposure apparatus according to claim 22, wherein the division can be carried out from different exposure media.

24. The exposure apparatus according to claim 1, wherein the feed line or a feed line system stands in connection with at least one device that treats the exposure medium.

25. The exposure apparatus according to claim 1, wherein the feed line and/or discharge line and/or a feed line system and/or a discharge line system of the respective line element are configured in such a manner that the exposure medium is conducted or conveyed through the well or over the biological test system in a controlled manner.

26. The exposure apparatus according to claim 25, wherein the discharge line or the discharge line system is provided with at least one connector for an apparatus that produces a partial vacuum.

27. The exposure apparatus according to claim 1, wherein the feed line and/or the discharge line or a feed line system and/or a discharge line system of the exposure apparatus can be connected or are connected with control elements for uniform distribution of the exposure medium to specific wells.

28. The exposure apparatus according to claim 1, wherein the exposure apparatus has one or more than one module or can be connected with one or more than one module, in such a manner that the exposure medium/media to be fed in and/or discharged can be subjected to physical, chemical or biological treatment.

29. The exposure apparatus according to claim 28, wherein the treatment of the exposure medium can be carried out in the same manner for all technical replicates or all specific wells, or differently for individual ones of the specific wells.

30. The exposure apparatus according to claim 28, wherein multiple treatment methods can be used in combination in a module, or only individually.

31. The exposure apparatus according to claim 28, wherein the one or more than one module for treatment is disposed ahead of and/or after a module for detection of the exposure medium/media to be fed in and/or discharged.

32. The exposure apparatus according to claim 1, wherein the exposure apparatus has one or more than one module or can be connected with one or more than one module, in such a manner that the exposure medium/media to be fed in and/or discharged and/or the biological test system can be subjected to physical, chemical or biological analysis.

33. The exposure apparatus according to claim 32, wherein the analysis of the exposure medium can be carried out in the same manner for all technical replicates or all specific wells, or differently for individual ones of the specific wells.

34. The exposure apparatus according to claim 32, wherein the multiple analysis methods can be used in combination in a module, or only individually.

35. The exposure apparatus according to claim 32, wherein the at least one module for analysis is disposed ahead of and/or after at least one module for treatment of the exposure medium/media to be fed in and/or discharged.

36. The exposure apparatus according to claim 32, wherein a module for physical, chemical or biological analysis can be carried out within and/or underneath the standard multiwell plate.

37. The exposure apparatus according to claim 1, wherein at least one well, a group of wells, or each well of a group stands in connection with a feed system and discharge system, by way of the line element assigned to a well, in each instance, composed of a feed line and discharge line, in such a manner that each well, each group of wells or each well of a group, individually, has an exposure medium with or without test substance flowing through it, at the same or different exposure volume streams.

38. The exposure apparatus according to claim 37, wherein at least one further volume stream is provided, aside from the exposure volume stream conducted into the well and out of the well, in each instance, by way of the line element, by way of which further volume stream, the exposure medium can be conducted through the exposure apparatus in the manner of pre-conveying, wherein exposure volume streams that can be predetermined can be conducted or fed out of this further volume stream.

39. The exposure apparatus according to claim 38, wherein the at least one further volume stream can be operated in the manner of pre-conveying, at a different volume flow rate than a sum of the individual exposure volume streams.

40. The exposure apparatus according to claim 37, wherein multiple further volume streams are provided, wherein exposure volume streams that can be predetermined can be brought into connection with each of the further volume streams.

41. The exposure apparatus according to claim 1, wherein one or more than one well of the standard multiwell plate has no line element assigned to the well or group of wells, wherein the well or this group of wells can be carried along in the in vitro experiment as a control sample.

42. The exposure apparatus according to claim 1, wherein one or more than one well has a line element assigned to the well or group of wells, in each instance, by means of which the exposure medium without test substance can be conducted to the well or this group of wells, and can be carried along in the in vitro experiment as a blind sample.

43. The exposure apparatus according to claim 1, wherein one or more than one well has a line element assigned to it, in each instance, by means of which the exposure medium with test substance can be conducted to the well or this group of wells, and can be carried along in the in vitro experiment as an actual sample.

44. The exposure apparatus according to claim 1, wherein a maintenance medium can be supplied to or is assigned to the standard multiwell plate, which medium stands in direct contact with an underside of a well or of a permeable carrier, on which underside or carrier the biological test system is disposed, to supply the biological test system.

45. The exposure apparatus according to claim 44, wherein the exposure apparatus has one or more than one module or can be connected with one or more than one module, in order to subject the maintenance medium or the maintenance medium/media that is/are fed in and/or discharged to physical, chemical or biological treatment.

46. The exposure apparatus according to claim 44, wherein the treatment of the maintenance medium can be carried out in the same manner for all technical replicates or for all specific wells, or differently for individual ones of the specific wells.

47. The exposure apparatus according to claim 44, wherein multiple treatment methods can be used in a module, in combination or only individually.

48. The exposure apparatus according to claim 44, wherein at least one module for treatment is disposed ahead of and/or after at least one module for detection of the maintenance medium or of the maintenance medium/media to be fed in and/or discharged.

49. The exposure apparatus according to claim 1, wherein the exposure apparatus has one or more than one module or can be connected with one or more than one module, in such a manner that the maintenance medium or the maintenance medium/media to be fed in and/or discharged can be subjected to a physical, chemical or biological analysis.

50. The exposure apparatus according to claim 49, wherein the analysis of the maintenance medium can be carried out in the same manner for all technical replicates or for all specific wells, or differently for individual ones of the technical replicates or specific wells.

51. The exposure apparatus according to claim 49, wherein the at least one module for analysis is disposed ahead of and/or after at least one module for treatment of the maintenance medium or of the maintenance medium/media to be fed in and/or discharged.

52. The exposure apparatus according to claim 49, wherein a module for physical, chemical or biological analysis can be carried out within or underneath the standard multiwell plate.

* * * * *

UNITED STATES PATENT AND TRADEMARK OFFICE
CERTIFICATE OF CORRECTION

PATENT NO. : 10,379,104 B2
APPLICATION NO. : 14/914139
DATED : August 13, 2019
INVENTOR(S) : Ritter et al.

It is certified that error appears in the above-identified patent and that said Letters Patent is hereby corrected as shown below:

On the Title Page

Item [73], should read:
--Fraunhofer-Gesellschaft zur Foerderung der angewandten Forschung e.V.--.

Item [22], should read:
--Aug. 29, 2014--.

Signed and Sealed this
Twelfth Day of November, 2019

Andrei Iancu
*Director of the United States Patent and Trademark Office*